(12) United States Patent
Biswas

(10) Patent No.: US 6,413,206 B2
(45) Date of Patent: Jul. 2, 2002

(54) INTRA-VAGINAL DEVICE

(75) Inventor: Nicholas Biswas, New South Wales (AU)

(73) Assignee: Niquoola Pty LTD, Baulkham Hills (AU)

( * ) Notice: Subject to any disclaimer, the term of this patent is extended or adjusted under 35 U.S.C. 154(b) by 0 days.

(21) Appl. No.: 09/197,736

(22) Filed: Nov. 20, 1998

(30) Foreign Application Priority Data

| Mar. 20, 1997 | (AU) | 97/00186 |
| Aug. 27, 1997 | (AU) | PO 8796 |
| Sep. 19, 1997 | (AU) | PO 9323 |
| Mar. 20, 1998 | (AU) | 98/00183 |

(51) Int. Cl.[7] .................................................. A61F 2/00
(52) U.S. Cl. ...................................................... 600/29
(58) Field of Search ..................... 128/885, DIG. 25; 600/29–31; 604/358–385.1

(56) References Cited

U.S. PATENT DOCUMENTS

| 1,790,801 | A |   | 2/1931 | Dickstein |
| 4,139,006 | A |   | 2/1979 | Corey |
| 4,920,986 | A |   | 5/1990 | Biswas |
| 5,036,867 | A | * | 8/1991 | Biswas ............... 600/29 X |
| 5,386,836 | A | * | 2/1995 | Biswas ............... 600/29 |
| 5,609,559 | A | * | 3/1997 | Weitzner ............. 600/29 |
| 5,618,256 | A | * | 4/1997 | Reimer .............. 600/29 |

FOREIGN PATENT DOCUMENTS

| DE | 37 20 858 | 1/1989 |
| EP | 0 264 258 | 4/1988 |
| EP | 0 460 807 | 12/1991 |

* cited by examiner

Primary Examiner—Samuel G. Gilbert
(74) Attorney, Agent, or Firm—Lyon & Lyon LLP

(57) ABSTRACT

An intra-vaginal device (30) to aid in controlling urinary incontinence. The device (30) has a base (31) from which there projects a rear part (34). The rear part (34) engages the posterior vaginal wall and rests on the pelvic floor and projects towards the cervix. The base (31) has a convex surface (33) which engages the anterior vaginal wall to support the vaginal wall and the urethra therebehind.

15 Claims, 6 Drawing Sheets

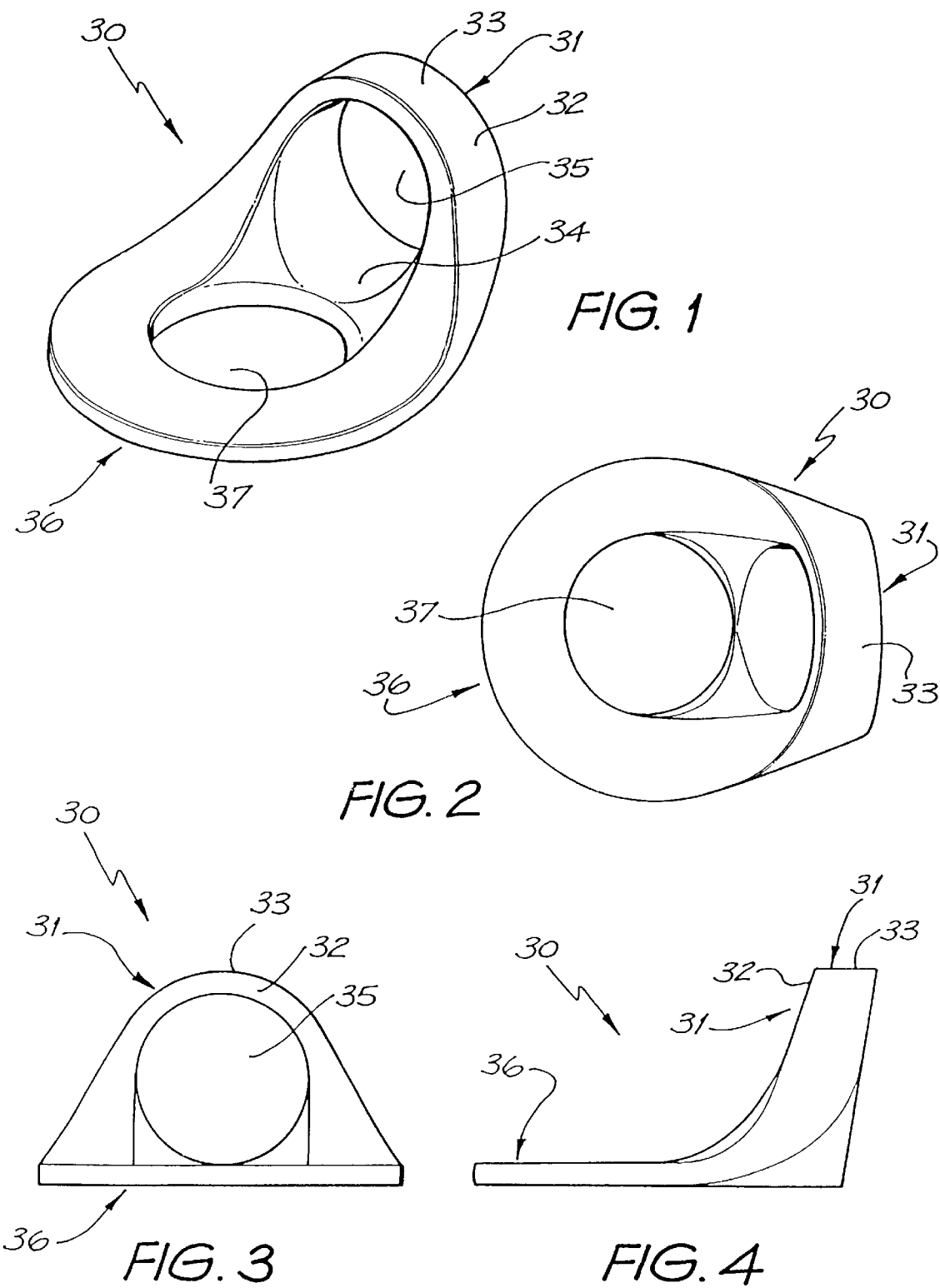

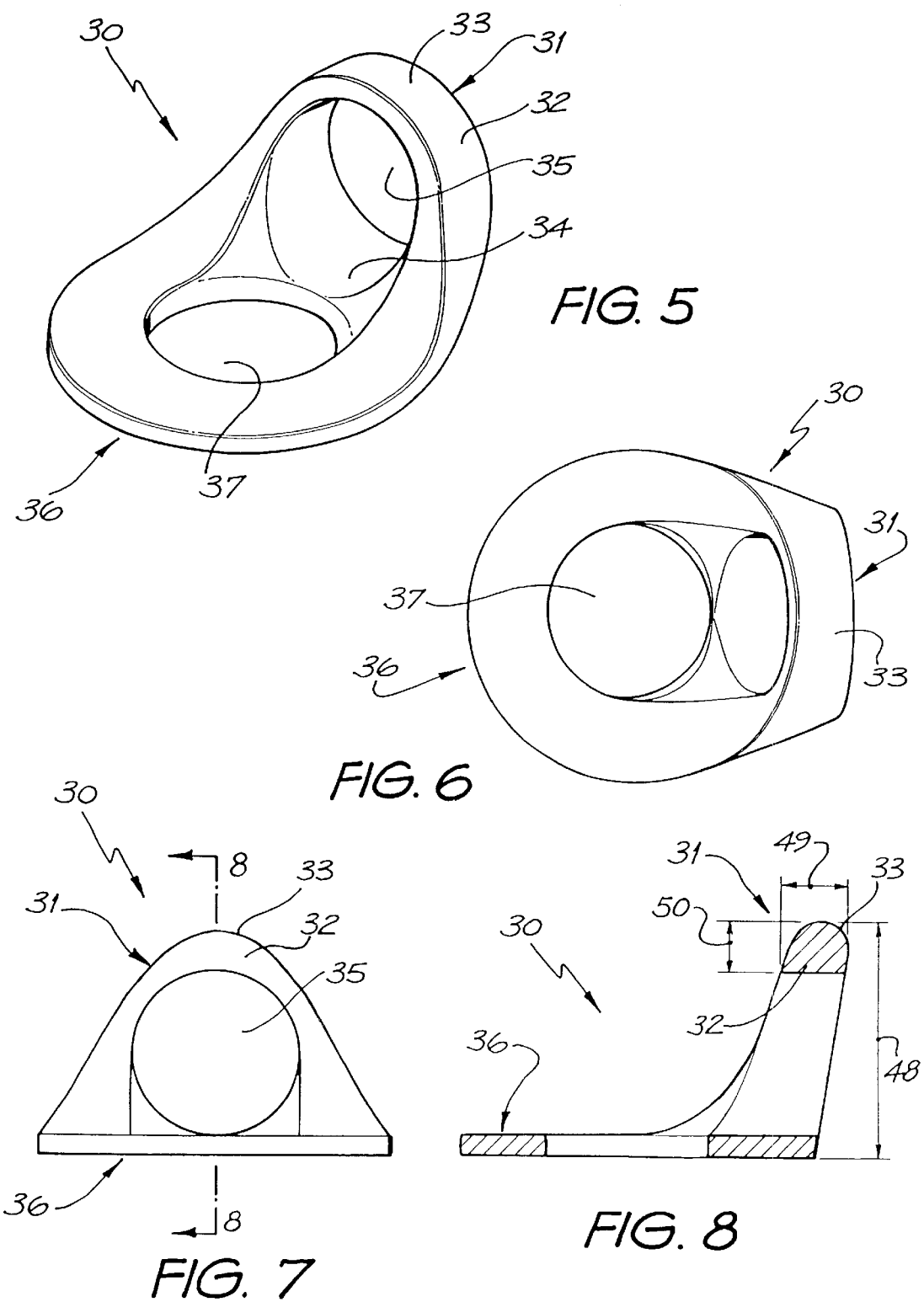

US 6,413,206 B2

1
INTRA-VAGINAL DEVICE

This application claims priority on International Application No. PCT/AU98/00183, filed Mar. 20, 1998, the disclosure of which is incorporated herein by reference, which relies for priority or International Application No. PCT/AU97/00186, filed Mar. 20, 1997, Australian Provisional Application No. P08796, filed Aug. 27, 1997 and Australian Provisional Application No. PO9323, filed Sep. 19,1997.

TECHNICAL FIELD

The present invention relates to intra-vaginal devices to aid in controlling urinary incontinence.

BACKGROUND OF THE INVENTION

Disclosed in U.S. Pat. No. 4,139,006 is an intra-vaginal device for controlling urinary incontinence in female patients. The device is slightly arcuate so as to have slightly raised anterior and posterior vaginal wall engaging portions with a lower central aperture. The anterior portion has a pair of projections generally within the plane of the. device which engage the vaginal wall to apply pressure to the urethra, to close the urethra. U.S. Pat. No. 5,036,867 and 4,920,986 also disclose intravaginal devices to aid in controlling urinary incontinence. However, these devices are arcuate in the opposite direction tot he previous device and engage the anterior vaginal wall to cradle the bladder neck. The urethra is not closed. U.S. Pat. No. 4,920,986 discloses a modification of the previous two devices but again the device cradles the bladder neck.

OBJECT OF THE INVENTION

It is the object of the present invention to at least partly correct hypermobility and augment urethrae support.

SUMMARY OF THE INVENTION

There is disclosed herein an intra-vaginal device to aid in controlling urinary incontinence, said device comprising:
 a base to extend between the anterior vaginal wall and the posterior vaginal wall of a patient, se as to apply pressure thereto, said base having a forward convex surface to engage the anterior vaginal wall to support and elevate the anterior vaginal wall and urthra without occluding the urethra, and a rear part to engage the posterior vaginal wall; and
 a back portion extending from said rear part so that in use it extends therefrom towards the cervix and is supported on the pelvic floor so as to distribute the pressure applied to the posterior wall.

BRIEF DESCRIPTION OF THE DRAWINGS

A preferred form of the present invention will now be described by way of example with reference to the accompanying drawings wherein:

FIG. 1 is schematic perspective view of an intra-vaginal device to aid in controlling urinary incontinence;

FIG. 2 is a schematic top plan view of the device of FIG. 1;

FIG. 3 is a schematic end elevation of the device of FIG. 1;

FIG. 4 is schematic side elevation of the device of FIG. 1;

FIG. 5 is schematic perspective view of a modified form of the device of FIG. 1;

FIG. 6 is schematic top plan view of the device of FIG. 5;

FIG. 7 is a schematic end elevation of the device of FIG. 5;

FIG. 8 is schematic side elevation of the device of FIG. 5;

DETAILED DESCRIPTION OF THE PREFERRED EMBODIMENTS

Figure 9:
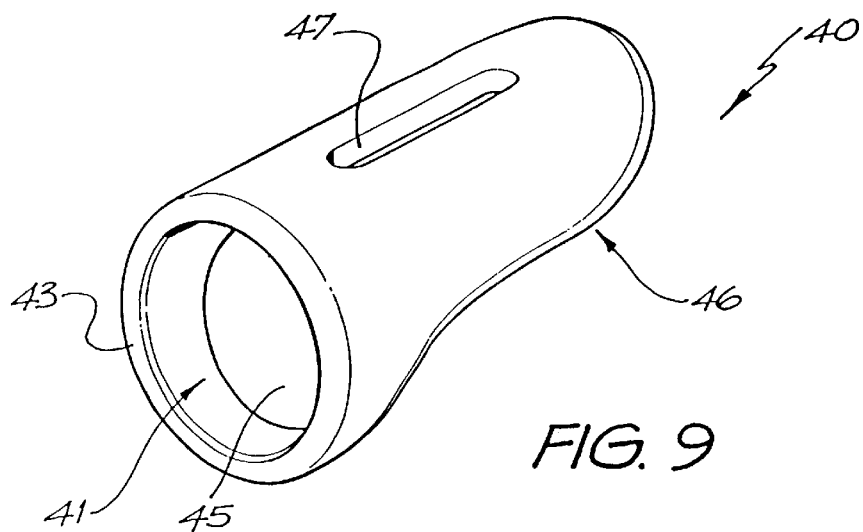
FIG. 9 is a schematic perspective view of a further device to aid in controlling urinary incontinence.
Figures 10, 12:
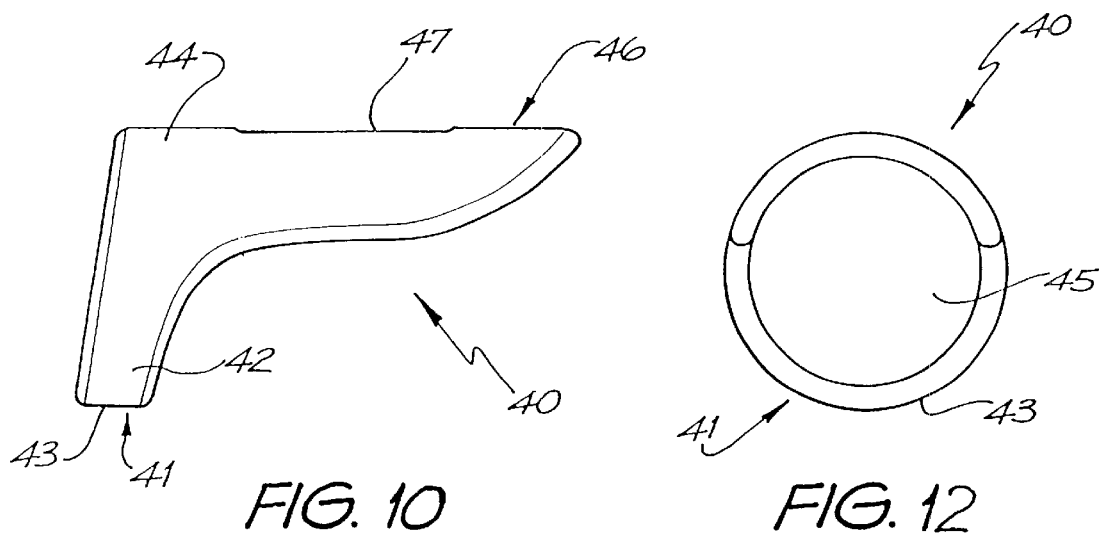
FIG. 10 is a schematic side elevation of the device of FIG. 9.
FIG. 12 is a schematic end elevation of the device of FIG. 9.
Figure 11:
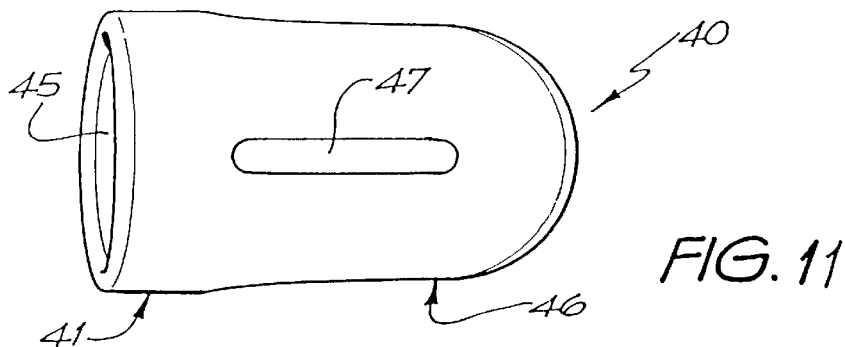
FIG. 11 is a schematic top plan view of the device of FIG. 9.
Figure 13:
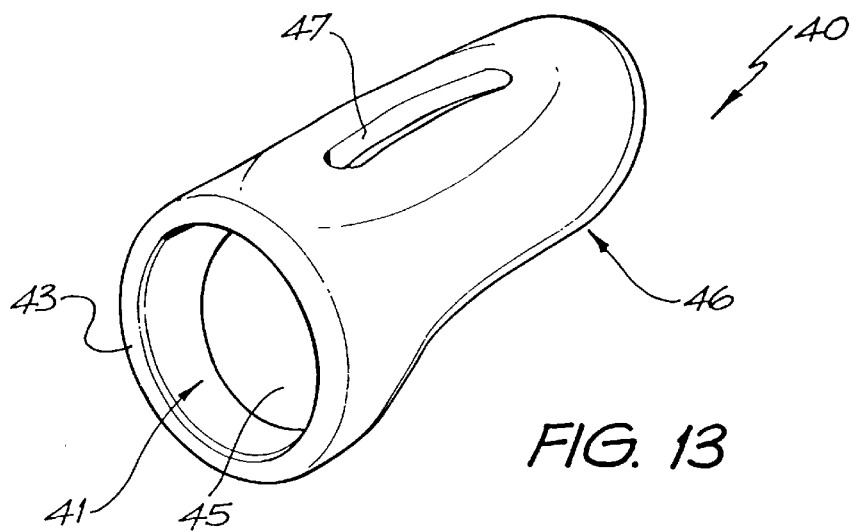
FIG. 13 is a schematic perspective view of a modified form of the device of FIG. 9.

The following embodiments are modifications and/or improvements in the devices described n international Application PCT/AU97/00186.

In FIGS. 1 to 8 of the accompanying drawings there is schematically depicted two intra-vaginal devices 30 to aid in controlling urinary incontinence. The devices 30 each include a base 31 having a forward arcuate part 32 with a forward convex surface 33 which engages the anterior wall to support and elevate the anterior vaginal wall and the urethra behind the vaginal wall. In that regard it should be appreciated that the devices 30 do not close the urethra. The base 31 is generally of a toroidal configuration and provides a rear part 34 and a central aperture 35.

Extending generally normal (that is at a slight inclination) to the base 31 and from the rear part 34 is a back portion 36 which is also generally of a toroidal configuration and has a central aperture 37. The base 31 and back portion 36 define a slightly obtuse included angle. In use, the back portion 36 engages the posterior vaginal wall and is supported by the pelvic floor and projects generally toward the cervix from the base 31. The base 31 extends between the posterior and anterior vaginal walls to apply supporting pressure thereto. The pressure applied to the posterior vaginal wall is distributed over the back portion 36.

Preferably the devices 30 would be formed of a resilient plastics material.

The above described preferred embodiments described with reference to FIGS. 1 to 8 is particularly suited for use by women with incontinence and prolapse with a poor pelvic floor.

With reference to the preferred embodiment of FIGS. 5 to 8, it should be appreciated that the surface 33 is not only convex as a result of consisting of a curve extending about the center of the aperture 35 (as best seen in FIG. 7) but may also be convex in a plane generally perpendicular thereto as best seen in the cross section of FIG. 8

The base has 31 a length 48 of between 35 mm and 55 mm, preferably within the range of 40 mm to 50 mm. The base 31 should also have a depth 49 of 1 to 3 cm, preferably 1.5 to 2.5 cm. Still further, the base 31 should have a thickness 50 of 3 to 6 mm, preferably 4 to 5 mm.

In FIGS. 9 to 16 of the accompanying drawings there are schematically depicted intra-vaginal devices 40 to aid in controlling urinary incontinence. Each device 40 has a base 41 provided with an arcuate forward part 42. The part 42 has a convex surface 43 which applies pressure to the anterior vaginal wall to support the vaginal wall and urethra therebehind. The base 31 is of a toroidal configuration having a central aperture 45.

Projecting generally normal from the base 41 is a back portion 46 which is generally "oval" in configuration. That is it has elongated sides terminating with an upper arcuate portion. The back portion 46 has a central slot 47. Again, the base 41 is slightly inclined to the back portion 46.

The base 41 extends between the anterior and posterior vaginal walls to apply pressure thereto. The pressure applied to the posterior vaginal wall is distributed over the back portion 46. The back portion 46 projects towards the cervix and is supported by the pelvic floor.

The device of FIGS. 9 to 16 is suitable for younger women with prolapse and urinary incontinence. Preferably it would be formed of an absorbent material so that it could also act as a tampon.

Figure 14:
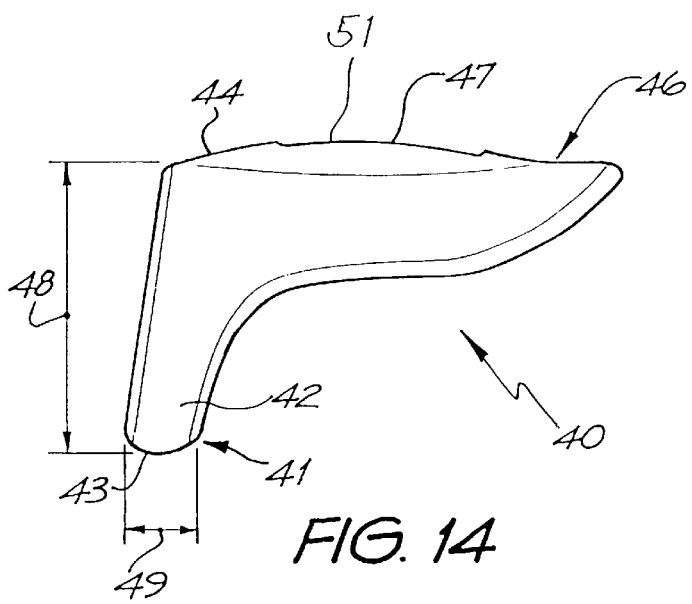
FIG. 14 is a schematic side elevation of the device of FIG. 13.
Figure 16:
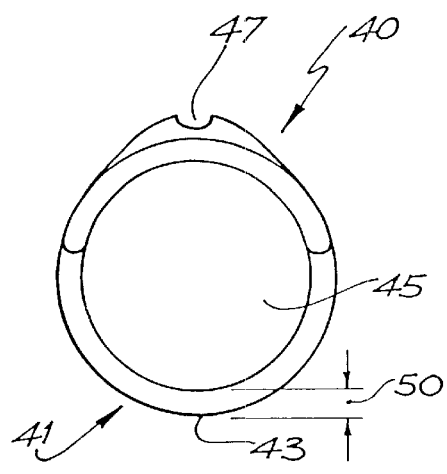
FIG. 16 is a schematic end elevation of the device of FIG. 13.
Figure 15:
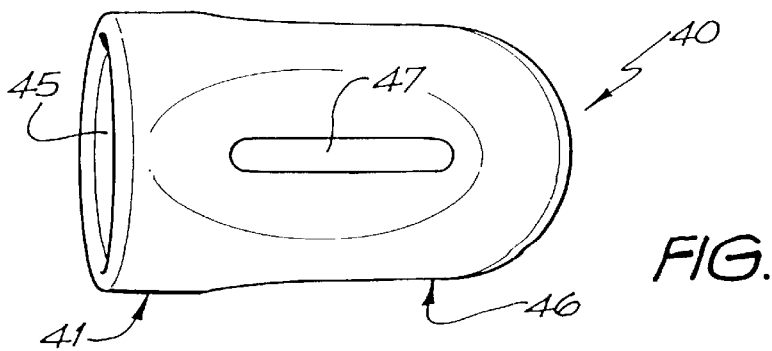
FIG. 15 is a schematic top plan view of the device of FIG. 13.

It should be appreciated in the embodiment of FIGS. 13 to 16 that the surface 43 is not oily convex as a result of consisting of a curve extending about the center of the aperture 35 (as best seen in FIG. 15) but may also be convex in a plane generally perpendicular thereto as best seen in FIG. 14.

The base 41 has a length 48 of between 35 mm and 55 mm, preferably within the range of 40 mm to 50 mm. The base 41 should also have a depth 49 of 1 to 3 cm, preferably 1.5 to 25 cm. Still further, the base 41 should have a thickness 50 of 3 to 6 mm, preferably 4 to 5 mm.

The rear surface 44 is also provided with an enlarged part 51 which is formed by shaping the rear surface 44 so as to be convex when viewed in side elevation (as best seen in FIG. 14). The rear surface 44, which engage the rear posterior vaginal wall, is also arcuate so as to be convex in a plane normal to the back portion 46.

The above two described embodiments address urinary incontinence problems previousy ameliorated by urethra pexy or sling procedure.

The above two described embodiments address the surfaces 33 and 43 apply pressure to the anterior vaginal wall adjacent the urethra so as to support and elevate the anterior vaginal wall and urethra located therebehind. This support and elevation occurs without occluding the urethra. In the above described two embodiments the dimensions 48 and 49 are arranged such that the force applied to the anterior vaginal wall is distributed to the extend that the urethra is not occluded but merely elevated and supported.

Figure 17:
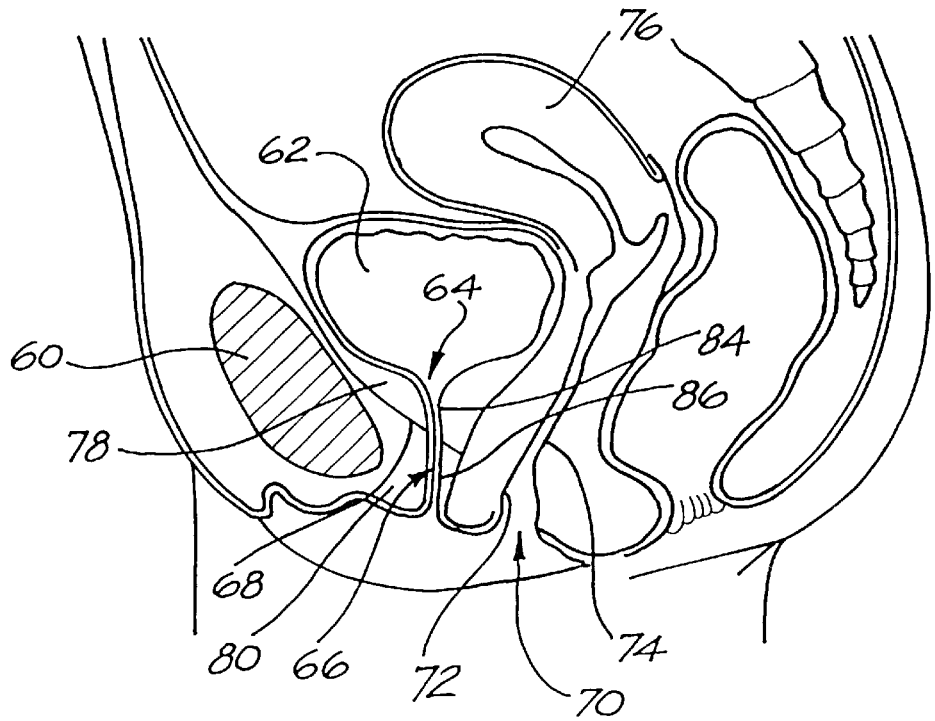
FIG. 17 is a sagital abdominal cross-sectional view of a female patient illustrating the normal physiology of the bladder and urethra.

FIG. 17 illustrates the normal anatomy of the urinary system of a female patient. Shown in FIG. 17 are the symphysis pubis 60; bladder 62 with bladder neck 64; urethra 66; pelvic floor 68; vagina 70 with anterior vaginal wall 72 and posterior vaginal wall 74; and uterus 76. Above the pelvic floor 68 is the abdominal cavity 78, with the vaginal cavity 80 lying below the pelvic floor.

Of particular note in FIG. 17 is the position of the bladder neck 64. The bladder 62 is located such that the bladder neck 64 is positioned above the pelvic floor 68. The upper portion 84 of the urethra 66 lies within the abdominal cavity 78, and the lower portion 86 of the urethra lies within the vaginal cavity 80. As a consequence of the upper portion 84 of the urethra 66 lying within the abdominal cavity 78, when dynamic abdominal pressure is exerted, such as by exercise or by coughing, the abdominal pressure is exerted not only on the bladder 62 but also on the upper portion 83 of the urethra 66. This transient pressure on the upper portion 84 of the urethra 66 balances the pressure exerted on the bladder 62 and thus helps prevent the leakage of urine despite transient increased bladder pressure.

Figure 18:
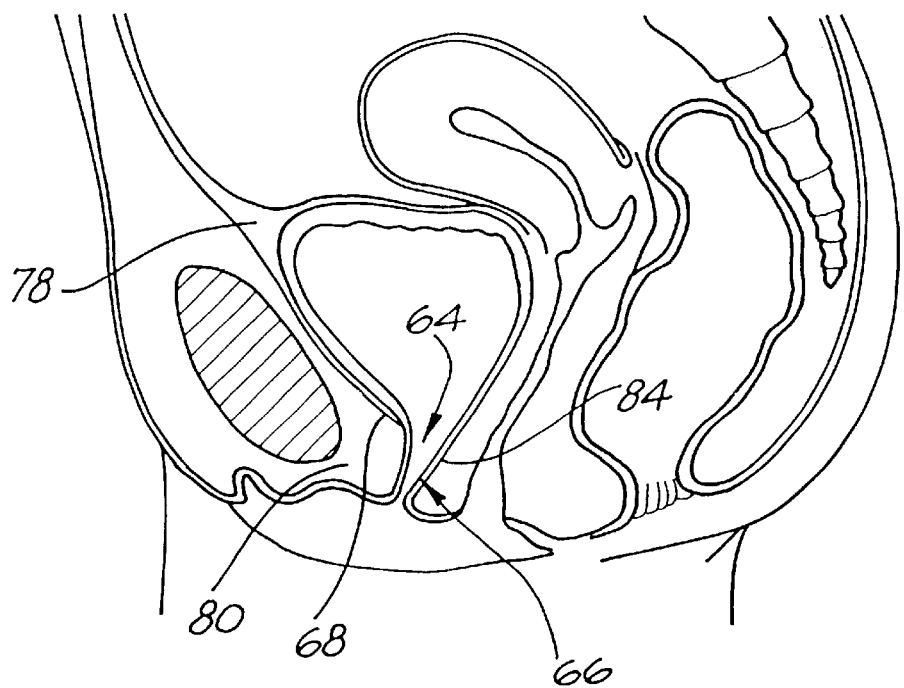
FIG. 18 is a sagital abdominal cross-sectional view of an incontinent female patient with the bladder neck in a descended position.

In FIG. 18, the bladder neck 64 has descended to a location at or below the pelvic floor 68. The entire urethra 66 lies within the vaginal cavity 80. In this condition, when dynamic abdominal pressure is exerted, because the upper portion 84 of the urethra 66 no longer lies within the abdominal cavity 78, there is no increased pressure exerted on the urethra 66 to offset the transient increased bladder pressure. Consequently, urine will leak when dynamic abdominal pressure is exerted, a condition known as stress urinary incontinence.

It will be appreciated that the condition illustrated in FIG. 18 can be either a static condition, such as when a cystocele condition exists, or a dynamic condition, which exists only in response to increased abdominal pressure. In a patient suffering the latter condition, the normal position of the bladder neck 64 in the absence of increased abdominal pressure may resemble that shown in FIG. 18. However, because of inadequate support, under increased abdominal pressure the bladder neck 64 will momentarily descend to a location at or below the pelvic floor 68, with the urine leakage consequences described above.

Figure 19:
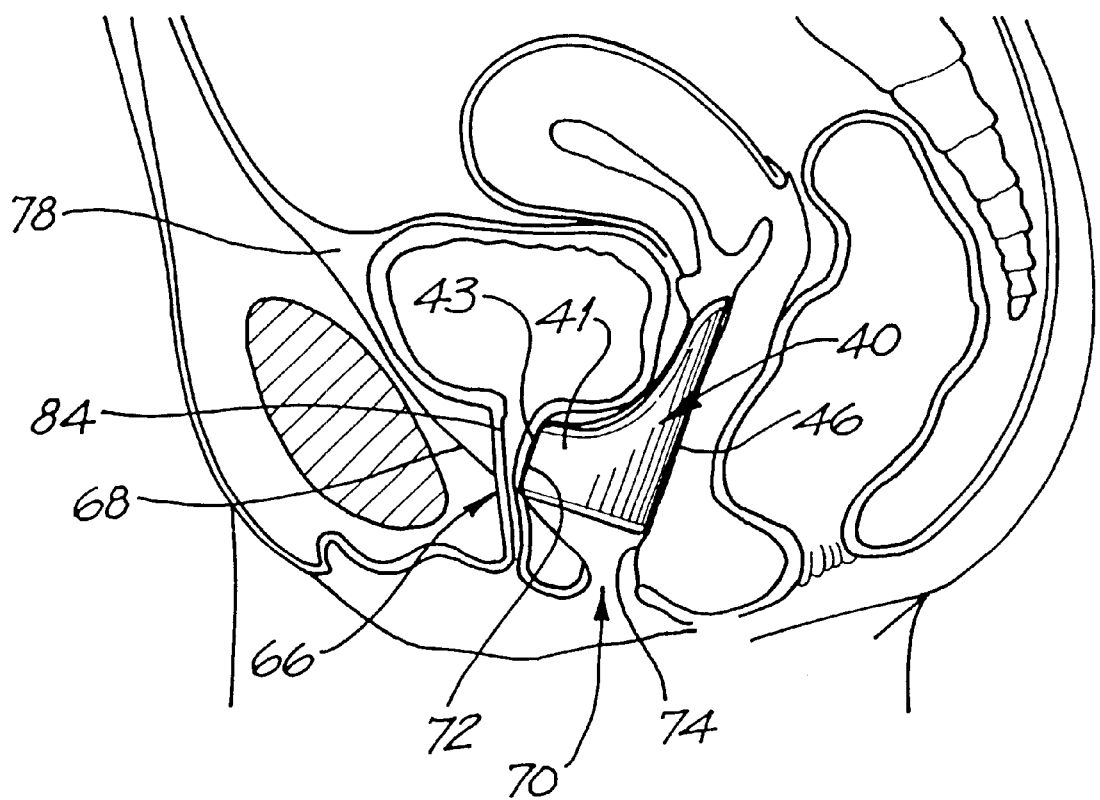
FIG. 19 is a sagital abdominal cross-sectional view of the female patient of FIG. 18 showing the device of FIGS. 13 to 16 installed.

FIG. 19 shows the device 40 installed to correct improper position of the urethra 66. While the figures show the use of the device 40, it is to be understood that the device 30 is installed and functions in the same general manner as to the device 40.

The back portion 46 of the device 40 rests on the posterior vaginal wall 74. The length and configuration of the back portion 46 of the device prevents the device from rotating or otherwise becoming displaced within the vagina 70. The lower end of the device 40 rests on the pelvic floor 68. With the device 40 installed in this position, the convex forward surface 43 of the base 41 of the device displaces the anterior vaginal wall 72 forward and upward to support the urethra 66. This support stabilises a hypermobile urethra such that the upper portion 84 of the urethra 66 is retained within the abdominal cavity 78. Consequently, when a dynamic abdominal pressure is exerted, a portion of the abdominal pressure is applied against the upper portion 84 of the urethra 66, which provides an additional force to offset transient bladder pressure increases.

In most adult female patients, it has been found that a device 40 in which the base 41 has a length 48 (see FIG. 14) of 35–55 millimeters, and most often 40–50 millimeters, will elevate the anterior wall 72 of the vagina 70 sufficiently to support the urethra 66 in the desired position. However, it will be appreciated that the length 48 of the device 40 needed to accomplish this result will depend on the physiology of the particular female patient, such that devices having a height of greater than 55 millimeters or less than 35 millimeters may be necessary to elevate the anterior vaginal wall 72 to support the urethra 66 in the proper position without occluding it, so long as the upper portion 84 of the urethra 66 is supported above the anterior segment of the pelvic floor 68 in a retropubic intra-abdominal position, continence should be achieve, thereby correcting hypermobility and augmenting urethrae support.

As will be a appreciated, the purpose of the devices 30, 40 is to support the urethra 66 without occluding it. Since exerting a force at single point along the length of the urethra 66 tends to have an occlusive effect, it is desirable to spread the support along a length of the urethra. Since the length of the urethra 66 of an adult female tends to be approximately 3 centimeters, an effective depth 49 (FIG. 14) for the convex forward end 43 of the base 41 of the device 40 has been found to be approximately 2.5 centimeters. However, it will be appreciated that a device 30, 40 having a forward edge 43 with a depth of as little as 1 centimeter may produce acceptable results so long as the effect of the supporting edge is to elevate the urethra to a retropubic intra-abdominal position without occluding it.

What is claimed is:

1. An intra-vaginal device to aid in controlling urinary incontinence, said device comprising:
    a base adapted to extend between the anterior vaginal wall and the posterior vaginal wall of a patient, so as to apply pressure thereto, said base having a forward convex surface adapted to engage the anterior vaginal wall to support and elevate the anterior vaginal wall and urethra, and a rear part adapted to engage the posterior vaginal wall; and
    a back portion extending from said rear part so that in use the back portion extends therefrom towards the cervix and is adapted to be supported on the pelvic floor so as to distribute the pressure applied to the posterior wall, said base being generally toroidal in configuration so as to have a central aperture.

2. The device of claim 1, wherein the back portion is inclined to the base so as to define an included obtuse angle slightly larger than 90°.

3. The device of claim 1, wherein the forward convex surface is arcuate both within the plane of the base and a plane generally perpendicular to the base.

4. The device of claim 3, wherein said back portion has a central slot.

5. The device of claim 1, wherein said back portion is generally of a toroidal configuration having a central aperture.

6. The device of claim 1, wherein said back portion has elongated sides extending from the base, which sides extend to an arcuate extremity.

7. The device of claim 6, wherein said back portion has a surface to engage the poster or vaginal wall, which surface is arcuate so as to be convex in a plane normal to the back portion.

8. The device of claim 6, wherein said back portion has an enlarged part which projects toward the posterior vaginal wall.

9. The device of claim 1 formed of resilient plastic material.

10. An intra-vaginal device to aid in controlling urinary incontinence, said device comprising:
    a base formed of an absorbent material so as to act as a tampon and extending between the anterior vaginal wall and the posterior vaginal wall of a patient, so as to apply pressure thereto, said base having a forward convex surface adapted to engage the anterior vaginal wall to support and elevate the anterior vaginal wall and urethra, and a rear part adapted to engage the posterior vaginal wall, and
    a back portion formed of an absorbent material so as to act as a tampon and extending from said rear part so that in use the back portion extends therefrom towards the cervix and is adapted to be supported on the pelvic floor so as to distribute the pressure applied to the posterior wall.

11. An intra-vaginal device to aid in controlling urinary incontinence, said device comprising:
    a base adapted to extend between the anterior vaginal wall and the posterior vaginal wall of a patient, so as to apply pressure thereto, said base having a forward convex surface adapted to engage the anterior vaginal wall to support and elevate the anterior vaginal wall and urethra, and a rear part adapted to engage the posterior vaginal wall; and
    a back portion extending from said rear part so that in use the back portion extends therefrom towards the cervix and is adapted to be supported on the pelvic floor so as to distribute the pressure applied to the posterior wall, the back portion being inclined to the base so as to define an inclined obtuse angle slightly larger than 90° and wherein the forward convex surface is arcuate both within the plane of the base and a plane generally perpendicular to the base, said base including a central aperture and being generally toroidal in configuration and said back portion including a back central aperture and being generally of a toroidal configuration.

12. The device of claim 11, wherein said back portion has elongated sides extending from the base, which sides extend to an arcuate extremity.

13. The device of claim 12, wherein said back portion has a surface to engage the posterior vaginal wall, which surface is arcuate so as to be convex in a plane normal to the back portion.

14. The device of claim 13, wherein said back portion has an enlarged part which projects toward the posterior vaginal wall.

15. An intra-vaginal device to aid in controlling urinary incontinence, said device comprising:
    a base formed of an absorbent material extending between the anterior vaginal wall and the posterior vaginal wall of a patient, so as to apply pressure thereto, said base having a forward convex surface adapted to engage the anterior vaginal wall to support and elevate the anterior vaginal wall and urethra, and a rear part adapted to engage the posterior vaginal wall, and
    a back portion formed of an absorbent material extending from said rear part so that in use the back portion extends therefrom towards the cervix and is adapted to be supported on the pelvic floor so as to distribute the pressure applied to the posterior wall, the back portion being inclined to the base so as to define an inclined obtuse angle slightly larger than 90° and wherein the forward convex surface is arcuate both within the plane of the base and a plane generally perpendicular to the base.

* * * * *